United States Patent
Fukuhara et al.

(10) Patent No.: US 11,253,295 B2
(45) Date of Patent: Feb. 22, 2022

(54) VERTEBRAL SPACER AND VERTEBRAL SPACER KIT

(71) Applicant: OLYMPUS TERUMO BIOMATERIALS CORP., Tokyo (JP)

(72) Inventors: Tomohiko Fukuhara, Shizuoka (JP); Koji Nishiyama, Tokyo (JP); Koichi Kuroda, Kanagawa (JP); Mitsuya Urata, Kanagawa (JP); Katsuyoshi Sobue, Tokyo (JP); Ryunosuke Seki, Fukuoka (JP)

(73) Assignee: OLYMPUS TERUMO BIOMATERIALS CORP., Tokyo (JP)

( * ) Notice: Subject to any disclaimer, the term of this patent is extended or adjusted under 35 U.S.C. 154(b) by 241 days.

(21) Appl. No.: 16/564,240

(22) Filed: Sep. 9, 2019

(65) Prior Publication Data
US 2020/0000499 A1     Jan. 2, 2020

Related U.S. Application Data

(63) Continuation of application No. PCT/JP2017/043386, filed on Dec. 4, 2017.

(30) Foreign Application Priority Data

Mar. 16, 2017    (JP) ............................. JP2017-051124

(51) Int. Cl.
*A61B 17/70*      (2006.01)
*A61F 2/44*      (2006.01)
(Continued)

(52) U.S. Cl.
CPC .............. *A61B 17/7071* (2013.01); *A61F 2/44* (2013.01); *A61B 17/86* (2013.01);
(Continued)

(58) Field of Classification Search
CPC ........ A61B 17/70; A61B 17/7071; A61F 2/44
See application file for complete search history.

(56) References Cited

U.S. PATENT DOCUMENTS

| | | | |
|---|---|---|---|
| 5,520,690 A | 5/1996 | Errico et al. | |
| 5,531,746 A | 7/1996 | Errico et al. | |

(Continued)

FOREIGN PATENT DOCUMENTS

| | | |
|---|---|---|
| EP | 3081179 B1 | 11/2017 |
| JP | 2003-284732 A | 10/2003 |

(Continued)

OTHER PUBLICATIONS

International Search Report dated Mar. 6, 2018 issued in PCT/JP2017/043386.

(Continued)

*Primary Examiner* — Christopher J Beccia
(74) *Attorney, Agent, or Firm* — Scully, Scott, Murphy & Presser, P.C.

(57) ABSTRACT

Provided is a vertebral spacer including a columnar main-body portion attached to individual cut end portions of the cut vertebral arch by screws, wherein the main-body portion is provided with two accommodating holes formed inside the main-body portion at positions spaced in a longitudinal direction of the main-body portion, and individually accommodating head portions of the screws, the individual accommodating holes are provided with openings through which the head portions are inserted into the accommodating holes from outside the main-body portion, and the openings have diameters greater than diameters of shaft portions of the screws, smaller than diameters of the head portions, and increased to a size that is greater than the diameters of the head portions.

11 Claims, 10 Drawing Sheets

(51) Int. Cl.
*A61B 17/86* (2006.01)
*A61F 2/30* (2006.01)

(52) U.S. Cl.
CPC .............. *A61F 2002/3054* (2013.01); *A61F 2230/0069* (2013.01); *A61F 2230/0071* (2013.01)

(56) References Cited

U.S. PATENT DOCUMENTS

| | | |
|---|---|---|
| 5,607,426 A | 3/1997 | Ralph et al. |
| 5,643,265 A | 7/1997 | Errico et al. |
| 5,647,873 A | 7/1997 | Errico et al. |
| 5,669,911 A | 9/1997 | Errico et al. |
| 5,690,630 A | 11/1997 | Errico et al. |
| 5,725,588 A | 3/1998 | Errico et al. |
| 5,817,094 A | 10/1998 | Errico et al. |
| 5,876,402 A | 3/1999 | Errico et al. |
| 5,882,350 A | 3/1999 | Ralph et al. |
| 2002/0045899 A1 | 4/2002 | Errico et al. |
| 2006/0217713 A1 | 9/2006 | Serhan et al. |
| 2006/0217714 A1 | 9/2006 | Serhan et al. |
| 2006/0217715 A1 | 9/2006 | Serhan et al. |
| 2008/0249625 A1 | 10/2008 | Waugh et al. |
| 2010/0106195 A1 | 4/2010 | Serhan et al. |
| 2010/0161056 A1 | 6/2010 | Voellmicke et al. |
| 2010/0185239 A1 | 7/2010 | Patel et al. |
| 2012/0143339 A1 | 6/2012 | Voellmicke et al. |
| 2013/0238094 A1* | 9/2013 | Voellmicke ........... A61F 2/4405 623/17.11 |
| 2014/0142699 A1* | 5/2014 | Beger ................ A61B 17/1757 623/17.11 |
| 2015/0039036 A1 | 2/2015 | Serhan et al. |
| 2016/0262740 A1* | 9/2016 | May ..................... A61B 17/025 |
| 2016/0296259 A1 | 10/2016 | Lee et al. |
| 2017/0027616 A1 | 2/2017 | Serhan et al. |
| 2017/0290613 A1 | 10/2017 | Lee et al. |
| 2019/0159811 A1 | 5/2019 | Serhan et al. |

FOREIGN PATENT DOCUMENTS

| | | |
|---|---|---|
| WO | 2006/104538 A1 | 10/2006 |
| WO | WO 2012/139905 A1 | 10/2012 |
| WO | WO 2016/167990 A1 | 10/2016 |

OTHER PUBLICATIONS

Indian Office Action dated Mar. 5, 2021 received in 201917039829.
Extended Supplementary European Search Report dated Dec. 3, 2020 in European Patent Application No. 17901053.3.
Korean Office Action dated Jan. 14, 2021 received in K.R. Patent Application No. 10-2019-7026470, 12 pages.

* cited by examiner

VERTEBRAL SPACER AND VERTEBRAL SPACER KIT

CROSS-REFERENCE TO RELATED APPLICATIONS

This is a continuation of International Application PCT/JP2017/043386, with an international filing date of Dec. 4, 2017, which is hereby incorporated by reference herein in its entirety. This application claims the benefit of Japanese Patent Application No. 2017-051124, filed on Mar. 16, 2017, the content of which is incorporated herein by reference.

TECHNICAL FIELD

The present invention relates to a vertebral spacer and a vertebral spacer kit.

BACKGROUND ART

In the related art, laminoplasty is known to be a treatment method for cervical spondylotic myelopathy, posterior longitudinal ligament ossification, yellow ligament ossification, and spinal disc herniation (for example, see Japanese Unexamined Patent Application, Publication No. 2003-284732). Laminoplasty is a method for increasing the diameter of the spinal canal by cutting a vertebral arch and by inserting a vertebral spacer between cut surfaces. As an attaching means for attaching the vertebral spacer inserted between cut surfaces to the vertebral arch, threads or screws are generally employed. In Japanese Unexamined Patent Application, Publication No. 2003-284732, as an attaching means that is an alternative to threads and screws, protrusions are provided on side surfaces of a vertebral spacer that comes into contact with cut surfaces of a vertebral arch, and the vertebral spacer is attached to the vertebral arch by inserting the protrusions into holes formed in the cut surfaces of the vertebral arch.

SUMMARY OF INVENTION

A first aspect of the present invention is a vertebral spacer including: a main-body portion that is columnar, that is disposed between cut end portions of a cut vertebral arch, and that is attached to the respective cut end portions by means of screws, wherein the main-body portion is provided with two accommodating holes that are formed inside the main-body portion at positions that are spaced in a longitudinal direction of the main-body portion, and that can individually accommodate head portions of the screws, the individual accommodating holes are provided with openings through which the head portions are inserted into the accommodating holes from outside the main-body portion, and the openings have diameters that are greater than diameters of shaft portions of the screws, that are smaller than diameters of the head portions, and that can be increased to a size that is greater than the diameters of the head portions.

DESCRIPTION OF EMBODIMENT

A vertebral spacer 1 according to an embodiment of the present invention and a vertebral spacer kit provided with the same will be described below with reference to the drawings.

Figure 1A:
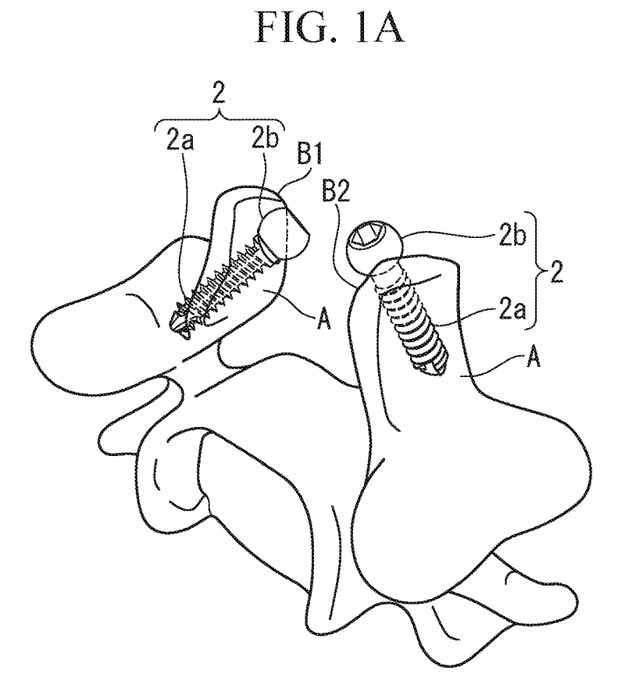
FIG. 1A is a diagram for explaining a method for using a vertebral spacer kit according to an embodiment of the present invention, and is a diagram showing a state in which screws are inserted into a vertebral arch on both sides of a cut position.
Figure 1B:
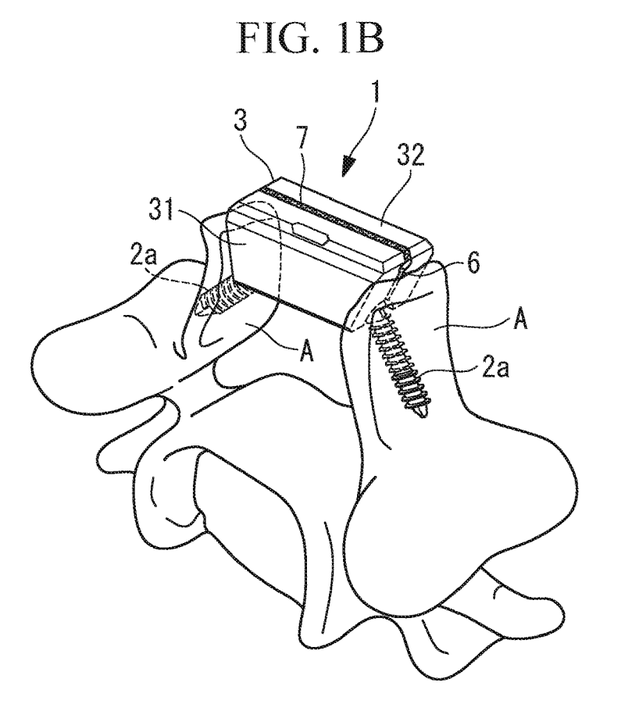
FIG. 1B is a diagram for explaining the method for using the vertebral spacer kit according to the embodiment of the present invention, and is a diagram showing a state in which a vertebral spacer is attached to the screws.

As shown in FIGS. 1A and 1B, the vertebral spacer kit according to this embodiment is used in laminoplasty in which a vertebral spacer 1 is attached to cut end portions B1 and B2 via screws 2 so that the vertebral spacer 1 is disposed between the cut end portions B1 and B2 of a vertebral arch A.

Figure 2:
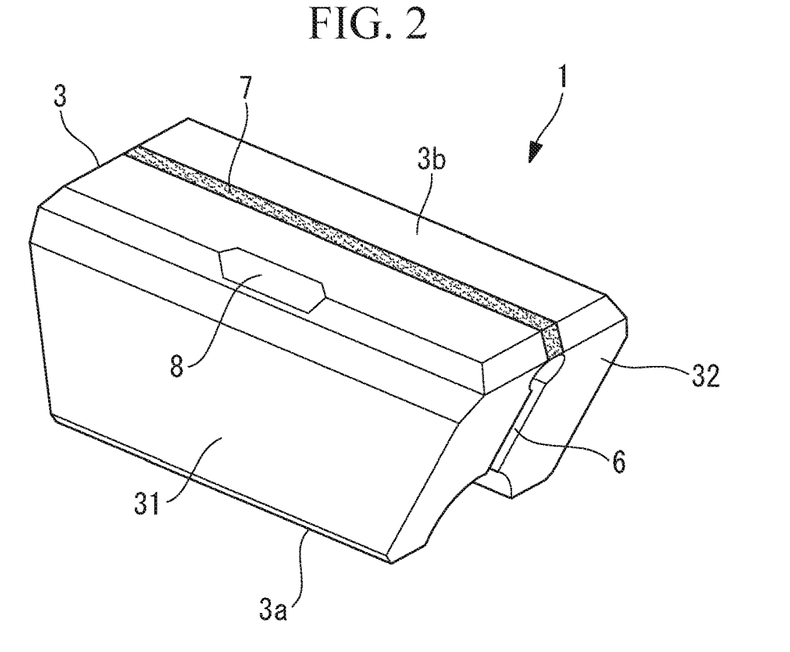
FIG. 2 is a perspective view showing the external appearance of the vertebral spacer according to the embodiment of the present invention.
Figure 3:
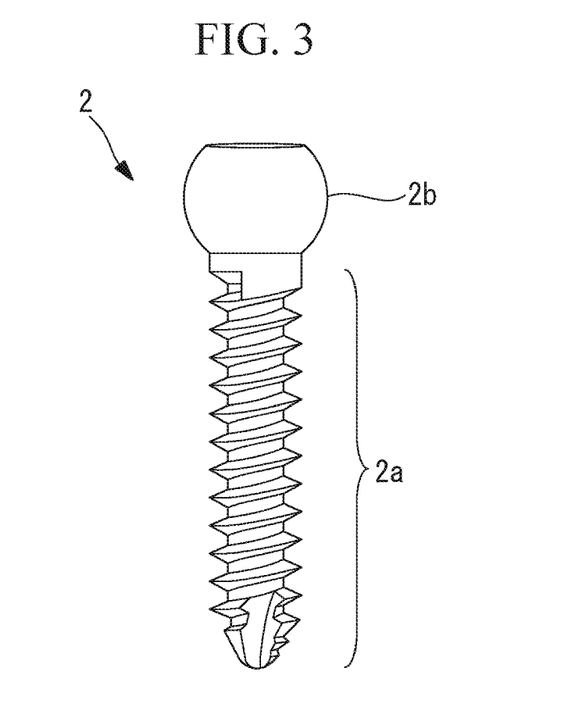
FIG. 3 is a side view of the screw according to the embodiment of the present invention.

The vertebral spacer kit according to this embodiment is provided with the vertebral spacer 1 shown in FIG. 2 and the two screws 2, one of which is shown in FIG. 3.

The screw 2 has a straight-rod-like shaft portion 2a in which a male screw is formed on an outer circumferential surface and a substantially spherical head portion 2b that is provided at one end of the shaft portion 2a and that has a greater diameter than the shaft portion 2a. The material for the screw 2 can arbitrarily be selected so long as the material possesses sufficiently high strength and biocompatibility. For example, the primary material for the screw 2 may be: stainless steel such as SUS316L (JIS registration number); a metal material such as pure titanium or a titanium alloy; or a polymer material such as PEEK (polyether ether ketone).

As shown in FIG. 2, the vertebral spacer 1 is provided with a rectangular-pillar-like main-body portion 3. Although FIG. 2 shows the main-body portion 3 in which end surfaces on both sides in the longitudinal direction are tilted in opposite directions with respect to the longitudinal direction, thus having trapezoidal side surfaces, the shape of the main-body portion 3 is not limited thereto. For example, the main-body portion 3 may be a cuboid having end surfaces that are parallel to each other or the main-body portion 3 may be cylindrical.

As with the material for the screw 2, the material for the main-body portion 3 can arbitrarily be selected so long as the material possesses sufficiently high strength and biocompatibility. For example, the primary material for the main-body portion 3 may be: stainless steel such as SUS316L (JIS registration number); a metal material such as pure titanium or a titanium alloy; or a polymer material such as PEEK.

Figure 4:
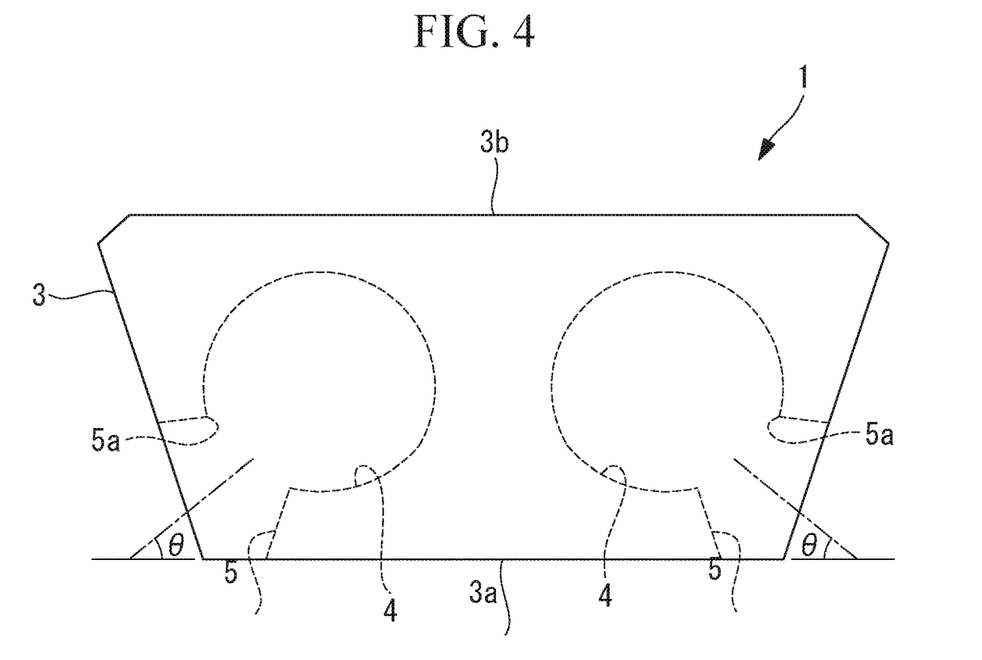
FIG. 4 is a side view of the vertebral spacer in FIG. 2.

As shown in FIG. 4, in the interior of the main-body portion 3, two substantially spherical accommodating holes 4 that have diameters that are slightly greater than the diameters of the head portions 2b and that are capable of accommodating the head portions 2b, and introducing holes 5 that are provided at the respective accommodating holes 4 and through which the shaft portions 2a of the screws 2 in which the head portions 2b thereof are accommodated in the accommodating holes 4 pass are formed.

The two accommodating holes 4 are provided with a spacing therebetween in the longitudinal direction of the main-body portion 3.

The introducing hole 5 is a substantially cylindrical hole in which one end thereof is open toward the accommodating hole 4 and the other end thereof is open at an end surface of the main-body portion 3 and/or a side surface (ventral surface) 3a that is disposed on a spinal-canal side (ventral side) when performing laminoplasty, and the interior of the accommodating hole 4 and the exterior of the main-body portion 3 are in communication via the introducing hole 5. An opening 5a at one end of the introducing hole 5 connected to the accommodating hole 4 has a diameter that is greater than the diameter of the shaft portion 2a and that is smaller than the diameter of the head portion 2b.

The introducing hole 5 has a substantially conical shape that has a center angle of about 45° and in which the inner diameter thereof gradually increases from one end to the other end. The head portion 2b can be rotated in an arbitrary direction in the accommodating hole 4 that is substantially spherical. Therefore, it is possible to change the orientation and the angle of the shaft portion 2a in the introducing hole 5 by pivoting the shaft portion 2a in the introducing hole 5 in a radial direction centered on the head portion 2b disposed in the accommodating hole 4. Specifically, the introducing hole 5 tolerates, within certain ranges, variations in the orientation and the angle of the shaft portion 2a that passes through the introducing hole 5.

It is preferable that angles θ formed by center axes of the introducing holes 5 with respect to the ventral surfaces 3a of the main-body portion 3 (see FIG. 4) be from −4° to 96° in consideration of the angles of the screws 2 to be inserted into the cut end portions B1 and B2 of the vertebral arch when performing laminoplasty. Specifically, the introducing holes 5 may extend substantially parallel to the longitudinal direction of the main-body portion 3 from the accommodating holes 4 toward the end surface of the main-body portion 3; the introducing holes 5 may extend substantially perpendicularly with respect to the ventral surfaces 3a from the accommodating holes 4 toward the ventral surfaces 3a; and the introducing holes 5 may be inclined toward the ventral surfaces 3a with respect to the longitudinal direction of the main-body portion 3. The two introducing holes 5 shown in FIG. 4 are formed at substantially equal angles θ so as to be substantially symmetrical with respect to the longitudinal direction of the main-body portion 3.

Figure 5:
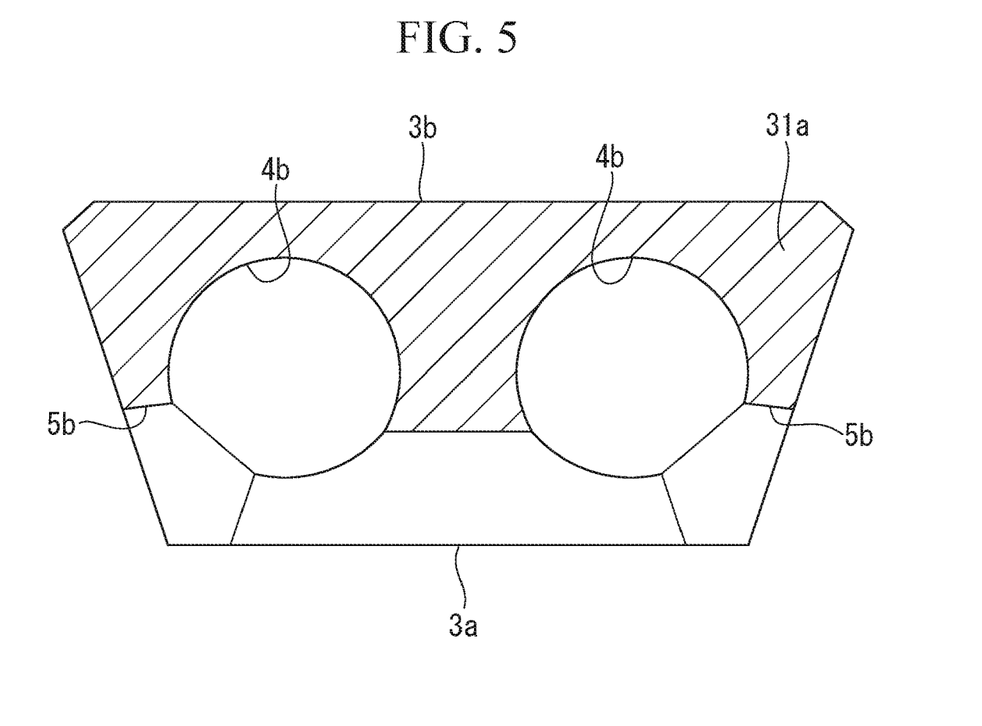
FIG. 5 is a diagram showing an inner surface of a first gripping piece of the vertebral spacer in FIG. 2.

The main-body portion 3 is formed with a groove 6 that divides the main-body portion 3 into two gripping pieces 31 and 32 in a direction that passes through the two accommodating holes 4 and the two introducing holes 5 and that intersects the main-body portion 3 in the longitudinal direction. The groove 6 is substantially parallel to the longitudinal direction of the main-body portion 3 and is formed over the entire length of the main-body portion 3 in the longitudinal direction from one end surface to the other end surface and is formed over the entire width from the ventral surfaces 3a to dorsal surfaces 3b facing the ventral surfaces 3a. The individual accommodating holes 4 and the individual introducing holes 5 are divided into substantially equal halves by the groove 6. Therefore, as shown in FIG. 5, in opposing inner surfaces 31a and 32a of the pair of gripping pieces 31 and 32, semispherical depressions 4b, which form the accommodating holes 4 are formed at positions at which the depressions 4b face each other, and substantially semiconical depressions 5b, which form the introducing holes 5, are formed at positions at which the depressions 5b face each other.

Figure 6A:
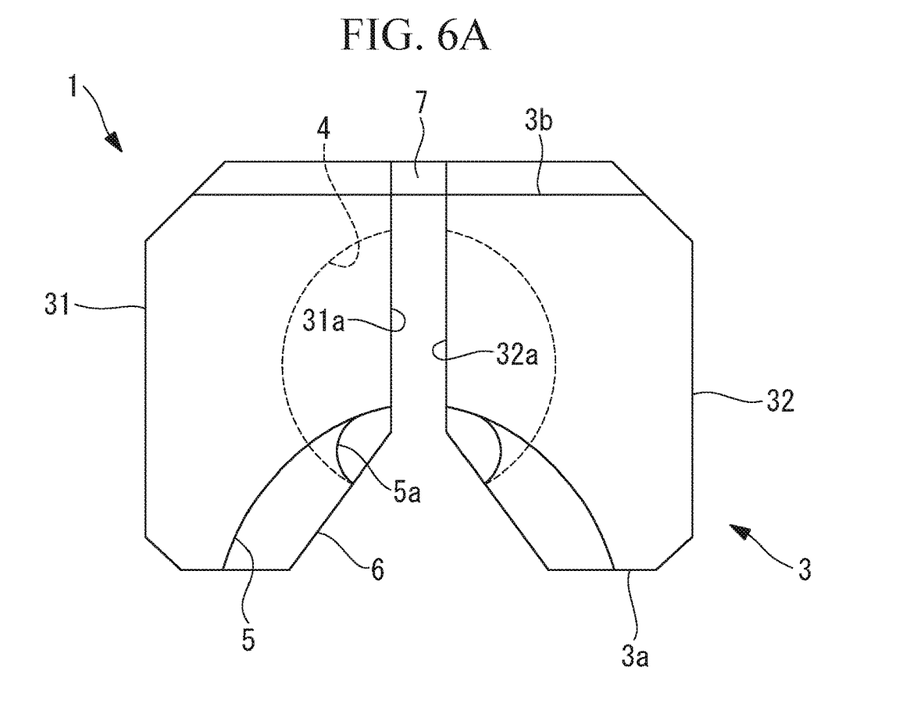
FIG. 6A is a front view viewed in the longitudinal direction, showing a closed state of the vertebral spacer in FIG. 2.
Figure 6B:
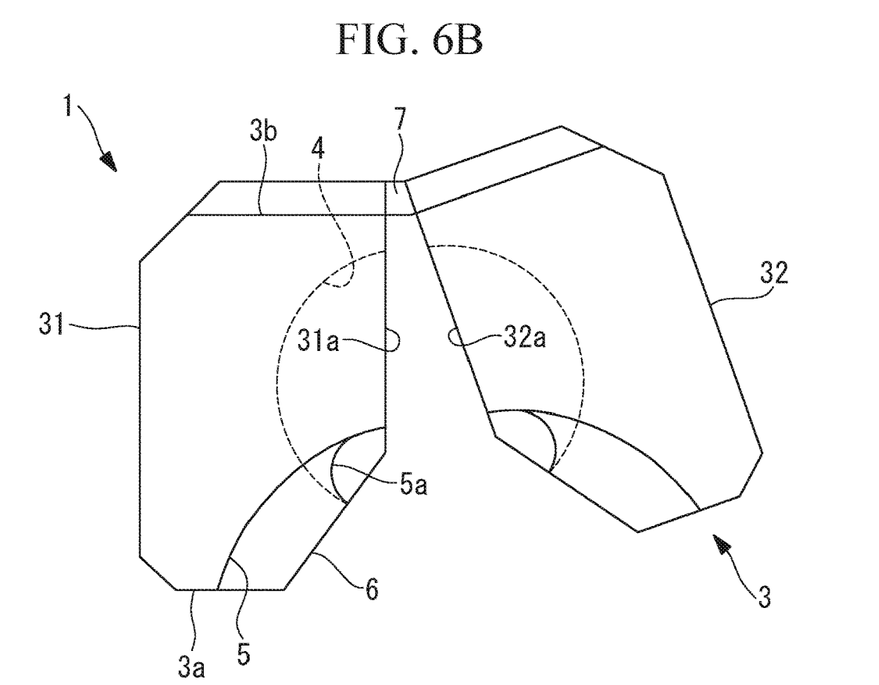
FIG. 6B is a front view viewed in the longitudinal direction, showing an open state of the vertebral spacer in FIG. 2.

A spring portion (holding portion, biasing member) 7 is provided at the dorsal surfaces 3b of the main-body portion 3, and the pair of gripping pieces 31 and 32 are linked with each other at the dorsal surfaces 3b by means of the spring portion 7, as shown in FIGS. 6A and 6B. As a result of the first gripping piece 31 and the second gripping piece 32 pivoting with respect to each other centered on the spring portion 7, the gripping pieces 31 and 32 can be opened/closed on the ventral surface 3a side.

The spring portion 7 is, for example, a thin member formed of an elastic material, and imparts a biasing force in a direction in which the pair of gripping pieces 31 and 32 are closed. Accordingly, the pair of gripping pieces 31 and 32 open/close in a clip-like manner. Specifically, in the normal state in which an external force in the opening direction is not acting on the pair of gripping pieces 31 and 32, the pair of gripping pieces 31 and 32 are held at the closed positions due to the biasing force of the spring portion 7, as shown in FIG. 6A. As a result of pivoting with respect to each other centered on the spring portion 7 while resisting the biasing force of the spring portion 7, the pair of gripping pieces 31 and 32 open with respect to each other, as shown in FIG. 6B. Here, as a result of opening the pair of gripping pieces 31 and 32, the groove width of the groove 6 (the spacing between the inner surfaces 31a and 32a) increases in the direction in which the pair of gripping pieces 31 and 32 face each other, and it is possible to increase the diameter of the opening 5a to a size that is greater than the diameter of the head portion 2b.

Although the operation of opening the pair of gripping pieces 31 and 32 may be performed by a surgeon by directly gripping the gripping pieces 31 and 32, the operation may be performed by using equipment. For example, an attachment hole 8 for attaching equipment (see FIG. 2) may be provided in a side surface of at least one of the gripping pieces 31 and 32. It would be possible for the surgeon to easily open the pair of gripping pieces 31 and 32 by operating the equipment attached to the attachment hole 8.

In portions that are closer to the dorsal surfaces 3b than the openings 5a are, the groove width of the groove 6 between the inner surfaces 31a and 32a in the state in which the pair of gripping pieces 31 and 32 are closed is smaller than the diameters of the head portions 2b so that the head portions 2b do not come out via the groove 6. The groove 6 is formed in a V-shape between the openings 5a and the ventral surfaces 3a so that the groove width of the groove 6 gradually increases toward the ventral surfaces 3a from the openings 5a. In this way, as a result of forming the inner surfaces of the groove 6 in the forms of inclined surfaces that are gradually separated from each other toward the ventral surfaces 3a from the openings 5a, it becomes easier to guide the head portions 2b toward the accommodating holes 4 from the ventral surface 3a side, and it is possible to easily insert the head portions 2b into the groove 6 even if the opening angle of the pair of gripping pieces 31 and 32 is small.

Next, the operation of the vertebral spacer kit according to this embodiment will be described in terms of an example of laminoplasty based on spinous-process longitudinal splitting in which a spinous process is longitudinally split. The vertebral spacer kit may be used in a one-side-opening type of laminoplasty, in which the vertebral arch is cut on one of the left and right sides, instead of the spinous-process longitudinal splitting.

In laminoplasty, a spinous process is longitudinally split, as shown in FIG. 1A, after cutting an end portion of the spinous process. Next, the screws 2 are individually inserted into the cut end portions B1 and B2 of the vertebral arch A from the cut-surface side.

Next, the pair of gripping pieces 31 and 32 are opened, and the pair of gripping pieces 31 and 32 are placed over the two screws 2 from the head-portion-2b side so that the head portions 2b are inserted into the accommodating holes 4 via the widened groove 6 and openings 5a. Next, the pair of gripping pieces 31 and 32 are closed by releasing the force applied to the pair of gripping pieces 31 and 32 in the opening direction. The pair of gripping pieces 31 and 32 are held in the closed state due to the biasing force of the spring portion 7. Accordingly, the vertebral spacer 1 is attached to the vertebral arch A between the cut end portions B1 and B2 via the two screws 2, as shown in FIG. 1B. The two head portions 2b accommodated in the two accommodating holes 4 of the vertebral spacer 1 are held at positions at which the two head portion 2b are separated from each other by a certain distance by the vertebral spacer 1. Therefore, it is possible to maintain the state in which the diameter of the spinal canal is increased by the vertebral spacer 1.

As has been described above, with this embodiment, two screws 2 are inserted into the cut end portions B1 and B2 of the vertebral arch A, and the vertebral spacer 1 is subsequently attached to the two head portions 2b so as to clamp the head portions 2b of the two screws 2. In this way, there is an advantage in that it is possible to attach the vertebral spacer 1 to the cut end portions B1 and B2 via the screws 2 in a simple manner with a one-touch operation as in a clip.

The positions, directions, and angles for inserting the screws 2 into the cut end portions B1 and B2 are not restricted by other members, and it is possible for the surgeon to freely select, within certain ranges, the positions, directions, and angles for inserting the screws 2. As a result of the accommodating holes 4 being substantially spherically formed, and the introducing holes 5 being formed so that the widths thereof gradually increase from the ends on the accommodating hole 4 side to the other ends, variations in the orientations and angles of the shaft portions 2a are tolerated within certain ranges. Therefore, the required precisions of orientations and angles are relaxed when inserting the screws 2 into the cut end portions B1 and B2. Accordingly, it is possible to more easily perform the insertion work of the screws 2.

Figure 7:
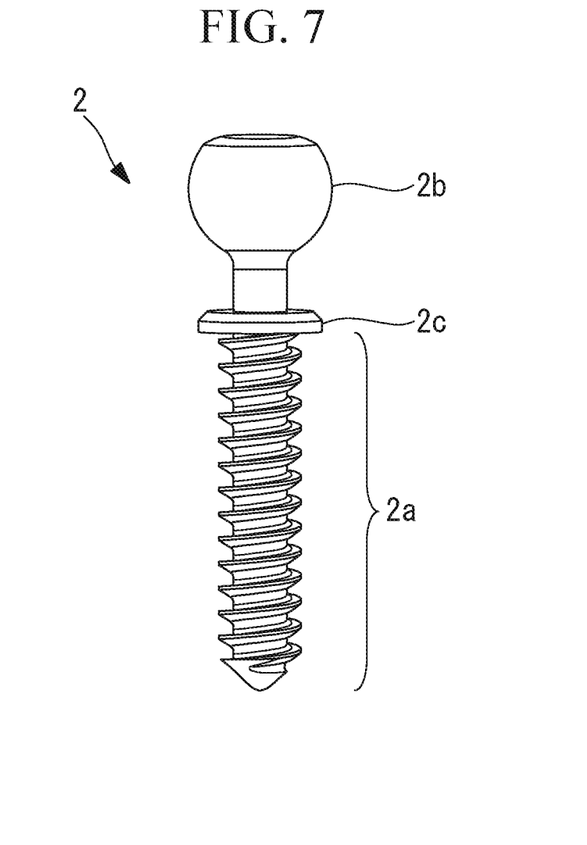
FIG. 7 is a side view showing a modification of the screw in FIG. 3.

In this embodiment, as shown in FIG. 7, the screw 2 may have, between the shaft portion 2a and the head portion 2b, an annular flange portion 2c that protrudes radially outward from the shaft portion 2a. It is preferable that the thickness of the flange portion 2c be about 0.3 to 1 mm.

As a result of inserting the shaft portion 2a of the screw 2 into the vertebral arch A until reaching a position at which the flange portion 2c abuts against a surface of the vertebral arch A, it is possible to control the amount by which the shaft portion 2a is inserted into the vertebral arch A so as to be constant. As a result of imparting an axial force in the longitudinal direction of the shaft portion 2a to the vertebral arch A from the flange portion 2c, it is possible to stabilize the fixing force of the screw 2 against the vertebral arch A by preventing the screw 2 from becoming loosened.

Figure 8A:
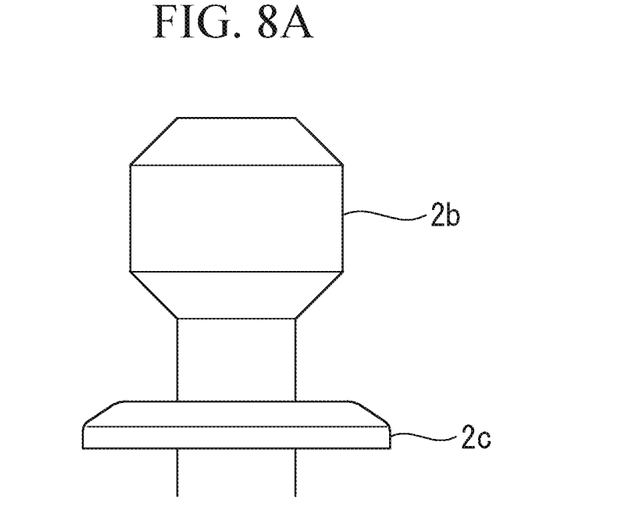
FIG. 8A is a side view showing a modification of the head portion of the screw.
Figure 8B:
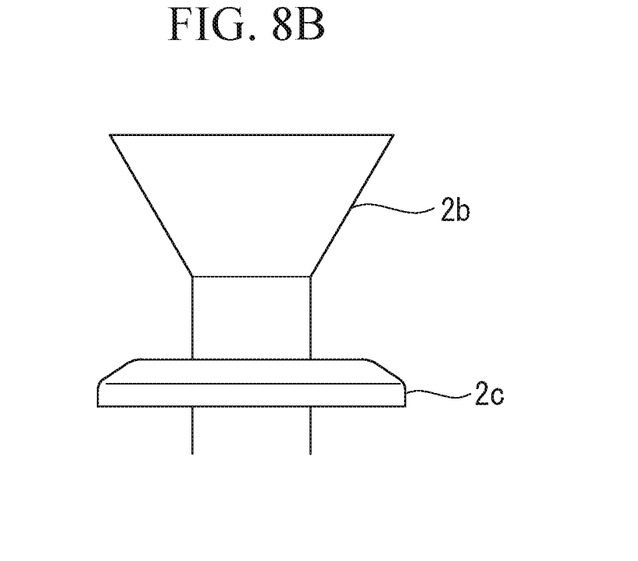
FIG. 8B is a side view showing another modification of the head portion of the screw.

In this embodiment, although the head portion 2b of the screw 2 is assumed to be substantially spherical, alternatively, other shapes may be employed. For example, the head portion 2b may be polyhedral, as shown in FIG. 8A, or frustum-shaped, as shown in FIG. 8B.

In this embodiment, although the accommodating hole 4 is assumed to be substantially spherical, the shape of the accommodating hole 4 may be another shape so long as the shape makes the accommodating hole 4 engage with the head portion 2b accommodated in the accommodating hole 4 in the axial direction and the direction intersecting the axial direction.

Figure 9:
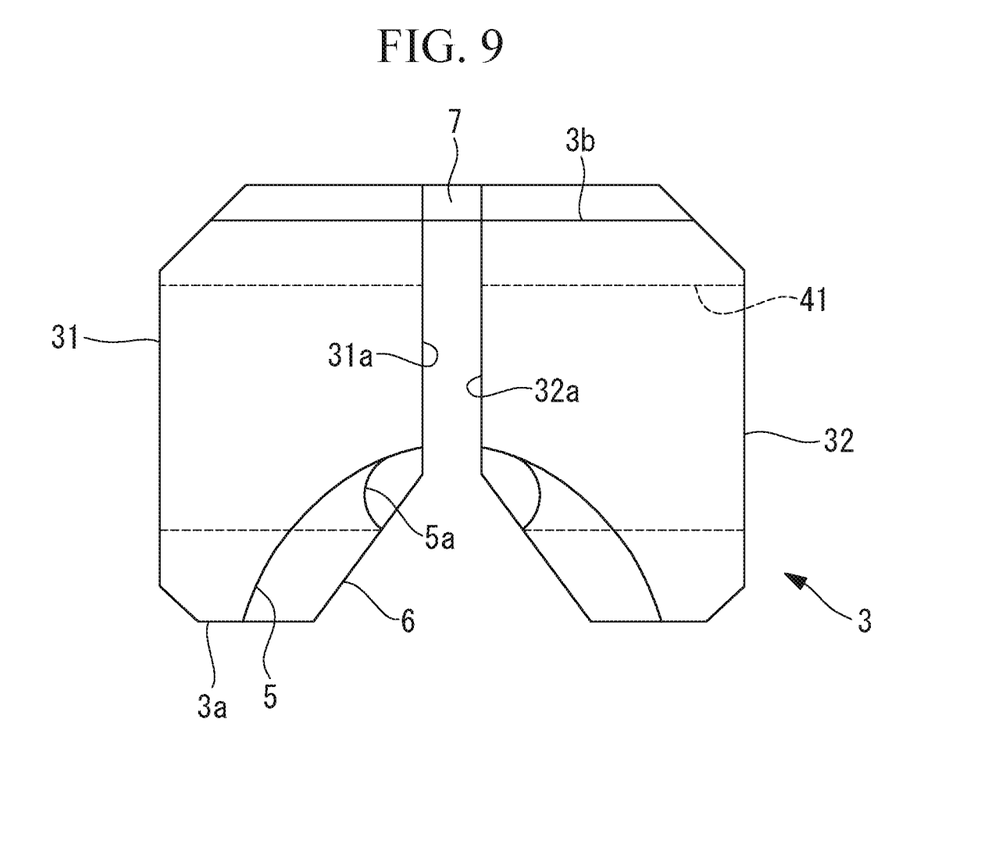
FIG. 9 is a front view viewed in the longitudinal direction, showing a modification of the vertebral spacer in FIG. 2.

For example, as shown in FIG. 9, an accommodating hole 41 may be cylindrical, substantially perpendicularly extending with respect to the inner surfaces 31a and 32a, and may pass through the gripping pieces 31 and 32. Alternatively, the shape of the inner surface of the accommodating hole 4 may be polyhedral or a shape that is complementary to the shape of the head portion 2b.

In this embodiment, although the pair of gripping pieces 31 and 32 are held at the closed positions by means of the biasing force of the spring portion 7, the holding portion for holding the pair of gripping pieces 31 and 32 at the closed positions is not limited thereto.

Figure 10:
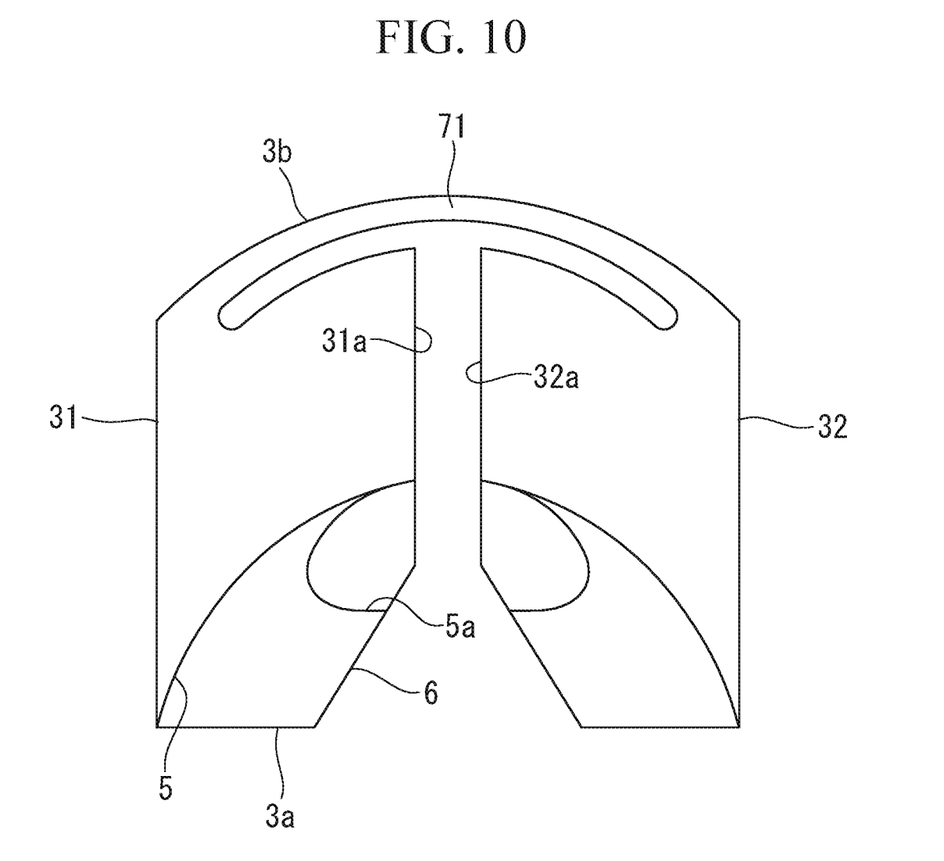
FIG. 10 is a front view viewed in the longitudinal direction, showing another modification of the vertebral spacer in FIG. 2.

As a first modification of the holding portion, as shown in FIG. 10, a deforming portion 71 that links the pair of gripping pieces 31 and 32 with each other and that plastically deforms in association with the closing operation of the pair of gripping pieces 31 and 32 may be employed, and the pair of gripping pieces 31 and 32 may be held at the closed positions by the plasticity of the plastically deformed deforming portion 71. The deforming portion 71 is formed of, for example, a thin region formed along the dorsal surfaces 3b of the main-body portion 3, as shown in FIG. 10.

Figure 11:
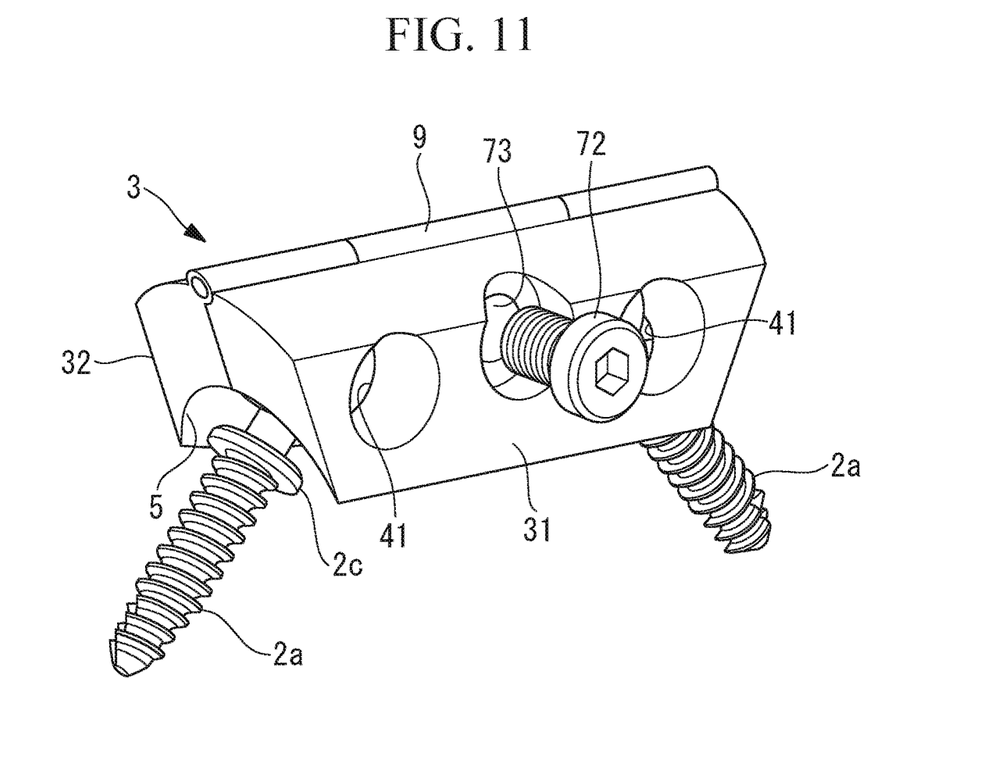
FIG. 11 is a perspective view showing another modification of the vertebral spacer in FIG. 2.

As a second modification of the holding portion, as shown in FIG. 11, a screw 72 that fastens the pair of closed gripping pieces 31 and 32 may be employed. Screw holes 73 that are in communication with each other in the closed state and through which the screw 72 is fastened are formed in the pair of gripping pieces 31 and 32.

As has been described above, in the case in which the screw 72 is used as the holding portion, the linkage mechanism, which links the pair of gripping pieces 31 and 32 in a manner in which the gripping pieces 31 and 32 can be opened/closed, is not required to generate a holding force for holding the pair of gripping pieces 31 and 32 at the closed positions. Specifically, the pair of gripping pieces 31 and 32 may be linked in a manner in which the gripping pieces 31 and 32 are freely opened/closed. For example, as shown in FIG. 11, the pair of gripping pieces 31 and 32 may be linked by means of a hinge 9 provided at the dorsal surfaces 3b so as to be freely pivotable with respect to each other.

Figure 12:
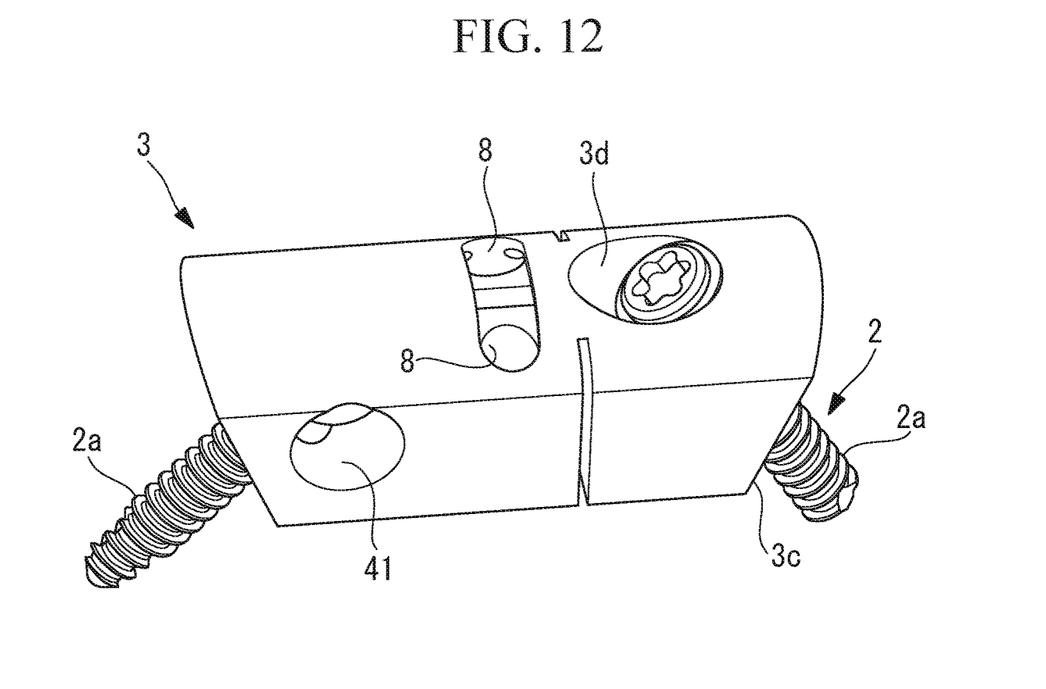
FIG. 12 is a perspective view showing another modification of the vertebral spacer in FIG. 2.

In this embodiment, although the main-body portion 3 has two accommodating holes 4, it suffices that at least one accommodating hole 4 be provided. FIG. 12 shows an example in which only one accommodating hole 4 is provided at one end portion of the main-body portion 3. In this case, an abutting portion 3c that is abutted against one of the cut end portions B1 and B2 is formed at the other end portion of the main-body portion 3.

The method for using the vertebral spacer in FIG. 12 will be described. After cutting the vertebral arch A, the screw 2 is inserted into the cut end portion B1, the head portion 2b of the screw 2 is accommodated in the accommodating hole 4, and thus, one end portion of the main-body portion 3 is connected to the cut end portion B1. Next, the abutting portion 3c at the other end portion of the main-body portion 3 is abutted against the other cut end portion B2, and the other end portion of the main-body portion 3 is secured to the cut end portion B2 by means of another screw 2. Therefore, a screw hole 3d in which the other screw 2 is fastened is provided at the other end portion of the main-body portion 3.

In this case, because it is possible to change, in the state in which the one end portion of the main-body portion 3 is connected to the cut end portion B1 via the screw 2, the orientation and the angle of the main-body portion 3 by moving the main-body portion 3 centered on the head portion 2b in the accommodating hole 4, it is possible to easily position the abutting portion 3c with respect to the other cut end portion B2.

Figure 13:
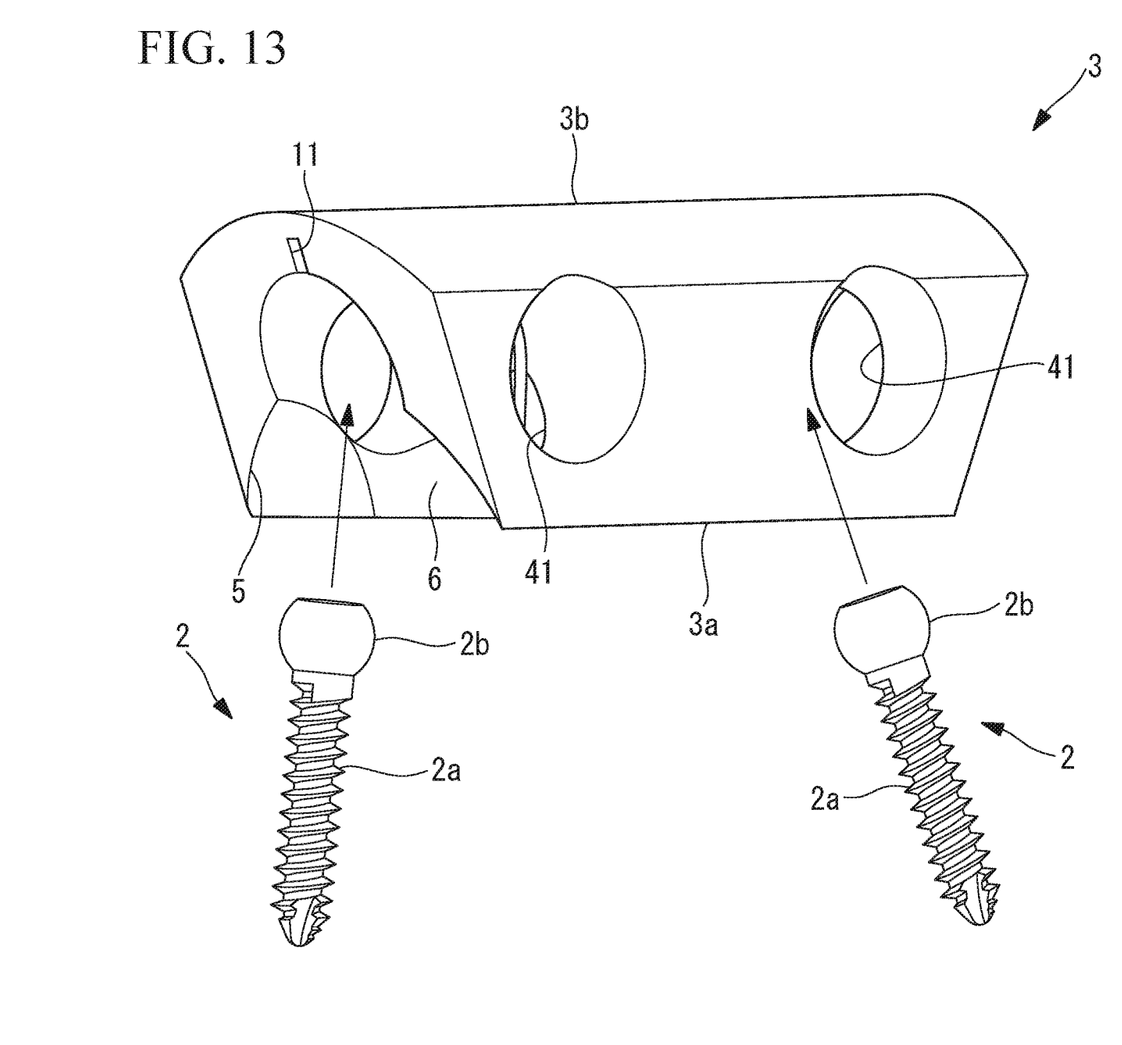
FIG. 13 is a perspective view showing another modification of the vertebral spacer in FIG. 2.

In this embodiment, although the main-body portion 3 is formed of the pair of gripping pieces 31 and 32 that are separated from each other by the groove 6 and that are linked in a manner in which the gripping pieces 31 and 32 can be opened/closed with respect to each other, alternatively, the main-body portion 3 may be formed of a single member, as shown in FIG. 13.

In the main-body portion 3 in FIG. 13, the groove 6 crosses over the accommodating holes 41 and ends at a position that is spaced from the dorsal surface 3b. In the main-body portion 3, the groove 6 and the openings 5a can be widened by using a portion between the end of the groove 6 and the dorsal surface 3b as a hinge and by opening the ventral surface 3a side by utilizing the elasticity of the hinge. Slits 11 that extend along the longitudinal direction may be formed in inner surfaces of the accommodating holes 41 on the dorsal-surface-3b side so as to make the opening operation of the main-body portion 3 easier.

With the vertebral spacer in FIG. 13, it is possible to press fit the head portion 2b into the accommodating hole 41 by sliding the head portion 2b into the groove 6 toward the accommodating hole 41 from the ventral-surface-3a side. Specifically, because the surgeon does not need to perform operations to open/close the pair of gripping pieces 31 and 32, it is possible to attach the vertebral spacer to the head portions 2b of the screws 2 inserted into the vertebral arch A with simpler operations.

Alternatively, a mechanism that causes elastic contraction in the radial direction of the head portion 2b may be provided in the head portion 2b of the screw 2. For example, a groove may be formed in a top surface of the head portion 2b, and the head portion 2b may be configured so that the head portion 2b contracts in the radial direction due to an external force that acts radially inward on an outer circumferential surface of the head portion 2b, and so that the outer diameter of the head portion 2b is restored when the external force is released.

By configuring the screw 2 in this way, when the head portion 2b is made to pass through the opening 5a in the contracted state, the head portion 2b undergoes self-expansion in the accommodating hole 4 after passing through the opening 5a, and thus, the head portion 2b is accommodated in the accommodating hole 4 in a manner in which the head portion 2b does not come out of the accommodating hole 4.

Figure 14:
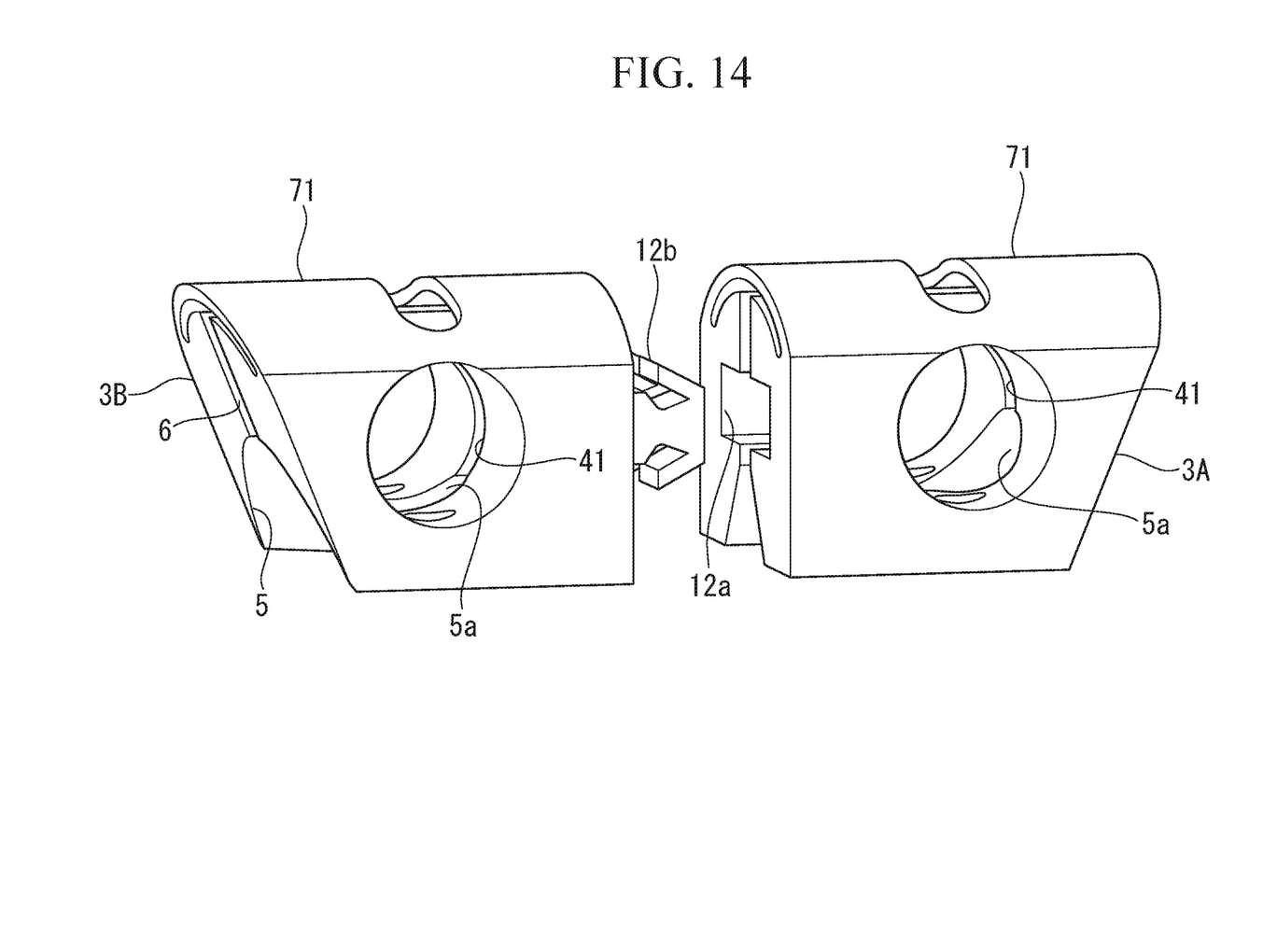
FIG. 14 is a perspective view showing another modification of the vertebral spacer in FIG. 2.

In this embodiment, although the main-body portion 3 is formed of a single unit, alternatively, as shown in FIG. 14, the main-body portion 3 may be formed of two units 3A and 3B each of which has one accommodating hole 41.

The two units 3A and 3B are provided with joining mechanisms for joining the two units 3A and 3B. It is preferable that the joining mechanisms be structures that are difficult to separate once the two units 3A and 3B are joined. For example, the joining mechanisms may be snap-fit structures formed of a depression 12a provided in the unit 3A and a protrusion 12b that is provided in the unit 3B and that is fitted into the depression 12a by utilizing elastic deformation. The two units 3A and 3B are separately attached to the head portions 2b of the two screws 2 inserted into the cut end portions B1 and B2 of the vertebral arch A, and are subsequently joined by means of the joining mechanisms 12a and 12b.

In this embodiment, although the vertebral spacer 1 is provided together with the screws 2 in the form of a vertebral spacer kit, alternatively, only the vertebral spacer 1 need be provided as a single item.

In this case, it is possible to use, in combination with the vertebral spacer 1, arbitrary screws having head portions that are suitable for the accommodating holes 4 of the vertebral spacer 1 in terms of size and shape.

As a result, the following aspect is read from the above described embodiment of the present invention.

A first aspect of the present invention is a vertebral spacer including: a main-body portion that is columnar, that is disposed between cut end portions of a cut vertebral arch, and that is attached to the respective cut end portions by means of screws, wherein the main-body portion is provided with two accommodating holes that are formed inside the main-body portion at positions that are spaced in a longitudinal direction of the main-body portion, and that can individually accommodate head portions of the screws, the individual accommodating holes are provided with openings through which the head portions are inserted into the accommodating holes from outside the main-body portion, and the openings have diameters that are greater than diameters of shaft portions of the screws, that are smaller than diameters of the head portions, and that can be increased to a size that is greater than the diameters of the head portions.

With the above-described first aspect, the openings of the two accommodating holes of the main-body portion are individually widened, the head portions are inserted into the accommodating holes via the openings, the diameters of the openings are subsequently reduced to sizes that are smaller than the diameters of the head portions, and thus, the head portions of the two screws are held by the main-body portion so as not to come out in the axial direction. Therefore, when performing laminoplasty, the main-body portion is attached to the two head portions in accordance with the above-described procedures so that the screws are individually inserted into the cut end portions on both sides of the vertebral arch and the two head portions protruding from the cut end portions are individually held in the accommodating holes, and thus, it is possible to dispose the main-body portion between the cut end portions and to attach the main-body portion to the cut end portions via the screws. Because a distance corresponding to the spacing between the two accommodating holes is maintained between the head portions of the two screws accommodated in the accommodating holes of the main-body portion, it is possible to continuously maintain a state in which the diameter of the spinal canal is increased.

In this way, the main-body portion is attached to the head portions of the screws after inserting the screws into the vertebral arch. Therefore, it is possible to insert the screws into the vertebral arch in a simple manner without restrictions from other members. It is possible to dispose the main-body portion between the cut end portions and to attach the main-body portion to the vertebral arch with a simple operation of merely fitting the head portions into the accommodating holes of the main-body portion.

In the above-described first aspect, the main-body portion may have a groove that is provided at a side surface of the main-body portion, that is formed in the longitudinal direction over the entire length of the main-body portion, and that passes through the two accommodating holes so as to divide the two accommodating holes in a direction that intersects the longitudinal direction, and wherein the groove may be capable of being widened in the direction that intersects the longitudinal direction.

By doing so, it is possible to increase the diameters of the openings that connect the groove and the accommodating holes by widening the groove.

In the above-described first aspect, the main-body portion may be provided with a pair of gripping pieces that are separated from each other by the groove and that are linked in a manner in which the gripping pieces can be opened/closed with respect to each other.

Because the openings are greatly widened by opening the pair of gripping pieces, it is possible to easily insert the head portions into the accommodating holes. After inserting the head portions into the accommodating holes, it is possible to hold the head portions in the accommodating holes by clamping the head portions between the pair of the gripping pieces by closing the pair of gripping pieces.

The above-described first aspect may be provided with a holding portion for holding the pair of gripping pieces at positions at which the gripping pieces are closed with respect to each other.

The holding portion may be provided with a biasing member that biases the pair of gripping pieces in a direction in which the gripping pieces are closed with respect to each other.

By doing so, because the pair of gripping pieces are held at the closed positions in a state in which an external force in the opening direction is not acting, it is not necessary to perform an operation for closing the pair of gripping pieces.

Alternatively, the holding portion may be provided with a deforming portion that plastically deforms in association with the closing operation of the pair of gripping pieces.

By doing so, the pair of closed gripping pieces are held at the closed positions due to the plasticity of the deforming portion. Specifically, with a single operation, it is possible to close the pair of gripping pieces and hold the gripping pieces at the closed positions.

In the above-described first aspect, the main-body portion may have substantially columnar introducing holes, each of which have one end provided at the accommodating hole via the opening and the other end provided in an outer surface of the main-body portion and through which the shaft portions of the screws in which the head portions thereof are accommodated in the accommodating holes pass, and the introducing hole may have an inner diameter that gradually increases toward the other end from the one end.

By doing so, variations in the directions and angles of the shaft portions passing through the introducing holes are allowed. Accordingly, it is possible to relax the required precisions of the directions and angles of the screws when inserting the screws into the vertebral arch.

In the above-described first aspect, the main-body portion may have a ventral surface that faces the spinal canal when disposed between the cut end portions, and angles formed between center axes of the introducing holes and the ventral surface may be −4° to 96°.

By doing so, it is possible to set the angles of the introducing holes to angles that are suitable for the angles of the shaft portions of the screws to be inserted into the cut end portions of the vertebral arch.

In the above-described first aspect, the accommodating holes may be substantially spherical.

By doing so, it is possible to accommodate head portions having arbitrary shapes in the accommodating holes. Because the substantially spherical accommodating holes and the head portions accommodated in the accommodating holes can be rotated in arbitrary directions relative to each other, it is possible to change, centered on the head portions accommodated in the accommodating holes, the orientation and the angle of the main-body portion with respect to the shaft portions of the screws.

A second aspect of the present invention is a vertebral spacer including: a columnar main-body portion that is disposed between cut end portions of a cut vertebral arch and that is attached to one of the cut end portions by means of a screw, wherein the main-body portion may be provided with a single accommodating hole that is formed inside the main-body portion and that can accommodate a head portion of the screw, and an abutting portion that is provided at a position spaced from the accommodating hole in the longitudinal direction of the main-body portion, and that is abutted against the other cut end portion, the accommodating hole may be provided with an opening through which the head portion is inserted into the accommodating hole from outside the main-body portion, and the opening may have a diameter that is greater than a diameter of the shaft portion of the screw, that is smaller than a diameter of the head portion, and that can be increased to a size that is greater than the diameter of the head portion.

With the above-described second aspect, when performing laminoplasty, the main-body portion is attached to the head portion so that the head portion of the screw inserted into one of the cut end portions of the vertebral arch is held in the accommodating hole, the abutting portion is abutted against the other cut end portion, and thus, it is possible to dispose the main-body portion between the cut end portions and attach the main-body portion to the one of the cut end portions via the screw. Because a distance corresponding to the spacing between the accommodating hole and the abutting portion is maintained between the one of the cut end portions, into which the screw is inserted, and the other cut end portion, against which the abutting portion is abutted, it is possible to continuously maintain a state in which the diameter of the spinal canal is increased.

In this way, the main-body portion is attached to the head portions of the screws after inserting the screws into the vertebral arch. Therefore, it is possible to insert the screws into the vertebral arch in a simple manner without restrictions from other members. It is possible to dispose the main-body portion between the cut end portions and to attach the main-body portion to the vertebral arch with a simple operation of merely fitting the head portions into the accommodating holes of the main-body portion and abutting the abutting portion against the other cut end portion.

A third aspect of the present invention is a vertebral spacer kit including: a vertebral spacer according to the above-described first aspect; and two screws, each of which has a shaft portion that is inserted into the cut end portion of the vertebral arch and a head portion that is provided at one end of the shaft portion and that has a greater diameter than that of the shaft portion.

In the above-described third aspect, the head portions of the screws may be substantially spherical.

By doing so, because the accommodating holes and the substantially spherical head portions accommodated in the accommodating holes can be rotated in arbitrary directions relative to each other, it is possible to change, centered on the head portions accommodated in the accommodating holes, the orientation and the angle of the main-body portion with respect to the shaft portions of the screws.

In the above-described third aspect, the screws may be provided with flange portions that are provided between the shaft portions and the head portions and that protrude radially outward from the shaft portions.

By doing so, as a result of inserting the screws into the vertebral arch until the flange portions abut against the vertebral arch, it is possible to control the amounts by which the screws are inserted into the vertebral arch to be constant. With axial forces that act on the vertebral arch from the flange portions, it is possible to increase the fixing force of the screws against the vertebral arch.

REFERENCE SIGNS LIST 1 vertebral spacer
2 screw
2a shaft portion
2b head portion
2c flange portion
3 main-body portion
31, 32 gripping piece
3a ventral surface
3b dorsal surface
3c abutting portion
3d screw hole
4, 41 accommodating hole
5 introducing hole
5a opening
6 groove
7 spring portion (biasing member, holding portion)
71 deforming portion (holding portion)
72 screw (holding portion)

The invention claimed is:

1. A vertebral spacer comprising:
a columnar main-body portion that is configured to be disposed between cut end portions of a cut vertebral arch and that is attached to the respective cut end portions by screws,
wherein the main-body portion is provided with two accommodating holes that are formed inside the main-body portion at positions that are spaced in a longitudinal direction of the main-body portion, and that individually accommodate head portions of the screws,
the individual accommodating holes are provided with openings through which the head portions are inserted into the accommodating holes from outside the main-body portion,
the openings have diameters that are greater than diameters of shaft portions of the screws, that are smaller than diameters of the head portions, and that are increased to a size that is greater than the diameters of the head portions,
the main-body portion has a groove that is provided at a side surface of the main-body portion, that is formed in the longitudinal direction over the entire length of the main-body portion, and that passes through the two accommodating holes so as to divide the two accommodating holes in a direction that intersects the longitudinal direction, and
the groove is widened in the direction that intersects the longitudinal direction.

2. A vertebral spacer according to claim 1, wherein the main-body portion is provided with a pair of gripping pieces that are separated from each other by the groove and that are linked in a manner in which the gripping pieces can be opened/closed with respect to each other.

3. A vertebral spacer according to claim 2, further comprising:
a holding portion that holds the pair of gripping pieces at positions at which the gripping pieces are closed with respect to each other.

4. A vertebral spacer according to claim 3, wherein the holding portion is provided with a biasing member that biases the pair of gripping pieces in a direction in which the gripping pieces are closed with respect to each other.

5. A vertebral spacer according to claim 3, wherein the holding portion is provided with a deforming portion that plastically deforms in association with the closing operation of the pair of gripping pieces.

6. A vertebral spacer comprising:
a columnar main-body portion that is configured to be disposed between cut end portions of a cut vertebral arch and that is attached to the respective cut end portions by screws,
wherein the main-body portion is provided with two accommodating holes that are formed inside the main-body portion at positions that are spaced in a longitudinal direction of the main-body portion, and that individually accommodate head portions of the screws,
the individual accommodating holes are provided with openings through which the head portions are inserted into the accommodating holes from outside the main-body portion,
the openings have diameters that are greater than diameters of shaft portions of the screws, that are smaller than diameters of the head portions, and that are increased to a size that is greater than the diameters of the head portions, and
the main-body portion has substantially columnar introducing holes, each of which has one end provided at the accommodating hole via the opening and the other end provided in an outer surface of the main-body portion and through which the shaft portions of the screws in which the head portions thereof are accommodated in the accommodating holes pass, and
the introducing hole has an inner diameter that gradually increases toward the other end from the one end.

7. A vertebral spacer according to claim 6,
wherein the main-body portion has a ventral surface configured to face the spinal canal when disposed between the cut end portions, and
angles formed between center axes of the introducing holes and the ventral surface are −4° to 96°.

8. A vertebral spacer according to claim 1, wherein the accommodating holes are substantially spherical.

9. A vertebral spacer kit comprising:
a vertebral spacer according to claim 1; and
two screws, each of which has a shaft portion that is configured to be inserted into the cut end portion of the vertebral arch and a head portion that is provided at one end of the shaft portion and that has a greater diameter than that of the shaft portion.

10. A vertebral spacer kit according to claim 9, wherein the head portions of the screws are substantially spherical.

11. A vertebral spacer kit according to claim 9, wherein the screws are provided with flange portions that are provided between the shaft portions and the head portions and that protrude radially outward from the shaft portions.

* * * * *